US012623994B2

(12) United States Patent (10) Patent No.: US 12,623,994 B2
Kim et al. (45) Date of Patent: May 12, 2026

(54) METHOD OF PREPARING HETEROGENEOUS LINEAR CARBONATE USING CATALYST HAVING EXCELLENT SOLUBILITY

(71) Applicant: LOTTE CHEMICAL CORPORATION, Seoul (KR)

(72) Inventors: Wang Gyu Kim, Daejeon (KR); Mi Hwa Baek, Daejeon (KR); Jong Myung Choi, Daejeon (KR); Eun Hye Han, Daejeon (KR); Jin Hyung Kim, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 456 days.

(21) Appl. No.: 18/253,887

(22) PCT Filed: Nov. 5, 2021

(86) PCT No.: PCT/KR2021/016036
§ 371 (c)(1),
(2) Date: May 22, 2023

(87) PCT Pub. No.: WO2022/114592
PCT Pub. Date: Jun. 2, 2022

(65) Prior Publication Data
US 2024/0002329 A1 Jan. 4, 2024

(30) Foreign Application Priority Data
Nov. 26, 2020 (KR) ........................ 10-2020-0161640

(51) Int. Cl.
| | |
|---|---|
| C07C 67/343 | (2006.01) |
| B01J 23/04 | (2006.01) |
| B01J 31/02 | (2006.01) |
| C07C 68/06 | (2020.01) |
| C07C 69/708 | (2006.01) |

(52) U.S. Cl.
CPC .............. C07C 68/06 (2013.01); B01J 23/04 (2013.01); B01J 31/0287 (2013.01); B01J 2231/49 (2013.01); B01J 2531/12 (2013.01)

(58) Field of Classification Search
CPC ........................... C07C 67/343; C07C 69/708
See application file for complete search history.

(56) References Cited

U.S. PATENT DOCUMENTS

| | | | |
|---|---|---|---|
| 6,831,028 B1 | 12/2004 | Ishii et al. | |
| 9,656,942 B2 * | 5/2017 | Ii ........................... | C07C 68/065 |

FOREIGN PATENT DOCUMENTS

| | | |
|---|---|---|
| CN | 103804124 A | 5/2014 |
| JP | H01317133 A | 12/1989 |
| JP | H0848539 A | 2/1996 |
| JP | 2005255517 A | 9/2005 |
| KR | 20110105379 A | 9/2011 |
| KR | 20120120075 A | 11/2012 |
| KR | 20150055022 A | 5/2015 |
| KR | 101668571 B1 | 10/2016 |
| KR | 101818614 B1 | 1/2018 |
| WO | 0228792 A1 | 4/2002 |

OTHER PUBLICATIONS

International Search Report issued in International Application No. PCT/KR2021/016036 dated Feb. 25, 2022 (2 pages).
Written Opinion issued in International Application No. PCT/KR2021/016036 dated Feb. 25, 2022 (4 pages).
Office Action issued in corresponding Japanese Patent Application No. 2023-532179, dated May 14, 2024, with translation (7 pages).

* cited by examiner

*Primary Examiner* — Bruck Kifle
(74) *Attorney, Agent, or Firm* — Osha Bergman Watanabe & Burton LLP

(57) ABSTRACT

The present invention relates to a method of preparing a heterogeneous linear carbonate, the method including performing a transesterification reaction of dimethyl carbonate (DMC) and ethanol (EtOH) in the presence of a catalyst, wherein the catalyst is one or more selected from the group consisting of lithium methoxide (LME), lithium ethoxide (LEE), sodium methoxide (SME), sodium hydroxide (NaOH), and a mixture thereof, and the catalyst is input in a state of being dissolved in a sulfoxide-based solvent.

7 Claims, No Drawings

METHOD OF PREPARING HETEROGENEOUS LINEAR CARBONATE USING CATALYST HAVING EXCELLENT SOLUBILITY

TECHNICAL FIELD

The present invention relates to a method of preparing a heterogeneous linear carbonate using a catalyst having excellent solubility.

BACKGROUND ART

It is well known that a method of preparing ethyl methyl carbonate (EMC) and diethyl carbonate (DEC), which are used as organic solvents for battery electrolytes, is through a transesterification reaction of dimethyl carbonate (DMC) and ethanol.

At this time, a catalyst is used for the reaction, and as the catalyst, sodium methoxide ($NaOCH_3$, SME) and sodium hydroxide (NaOH), which have excellent activity, are mainly used. However, since the SME or NaOH has low solubility in organic solvents and is insoluble in DMC, EMC, and DEC, it causes column plugging in a reactive distillation process or a purification process, so that process trouble occurs.

In this regard, in Patent Document 1, EMC and DEC are prepared through a reactive distillation method using DMC, an alcohol, and a catalyst. Referring to the drawings, there is a strainer at the rear of a reactive distillation column to separate the solid phase, but when the alcohol is distilled in the reactive distillation column, the catalyst is eventually precipitated, so that powder builds up on the packing inside the column and still causes plugging.

In addition, Patent Document 2 discloses that DEC is produced at a high rate by utilizing the SME catalyst and reactive distillation, wherein the inside of a reactive distillation column is composed of a porous tray, the catalyst is input in a mixed state of SME and an alcohol such as ethanol, but in this method, after the alcohol is distilled inside the reactive distillation column, the catalyst is precipitated from the bottom concentrate, causing plugging, and even if the catalyst passes to the downstream separation process, not only problems are expected inside an EMC purification tower, but also during DEC purification, there is a problem of loss of DEC due to precipitated SME.

Therefore, there is a need for research on a method for effectively preparing a heterogeneous linear carbonate for a battery electrolyte by solving the above problems.

RELATED ART DOCUMENTS

Patent Documents (Patent Document 1) Chinese Patent Publication No. 103804124
(Patent Document 2) Korean Patent Publication No. 10-1668571

DISCLOSURE

Technical Problem

The present invention is directed to providing a method a preparing a heterogeneous linear carbonate, wherein the method uses a sulfoxide-based solvent with excellent catalyst solubility, and the catalyst does not precipitate even in a purification process, thereby reducing maintenance costs and having excellent economic efficiency because the catalyst can be reused.

Technical Solution

One embodiment of the present invention provides a method of preparing a heterogeneous linear carbonate, the method including performing a transesterification reaction of dimethyl carbonate (DMC) and ethanol (EtOH) in the presence of a catalyst, wherein the catalyst is one or more selected from the group consisting of lithium methoxide (LME), lithium ethoxide (LEE), sodium methoxide (SME), sodium hydroxide (NaOH), and a mixture thereof, and the catalyst is input in a state of being dissolved in a sulfoxide-based solvent.

Advantageous Effects

A method of preparing a heterogeneous linear carbonate according to the present invention minimizes process problems by effectively preventing catalyst precipitation during a distillation process to prevent column plugging by inputting a catalyst in a state of being dissolved in a sulfoxide-based solvent having excellent catalyst solubility during a transesterification reaction, and thus has effects of reducing maintenance costs and remarkably improving the reuse efficiency of the catalyst.

Modes of the Invention

Throughout the specification, when a part is said to "include" a component, this means that the part may further include other components rather than excluding other components unless specifically stated to the contrary.

In the present specification, the unit "% by weight" may mean the ratio of the weight of a certain component to all components.

Hereinafter, the present invention will be described in detail.

One embodiment of the present invention provides a method of preparing a heterogeneous linear carbonate, the method including performing a transesterification reaction of dimethyl carbonate (DMC) and ethanol (EtOH) in the presence of a catalyst, wherein the catalyst is one or more selected from the group consisting of lithium methoxide (LME), lithium ethoxide (LEE), sodium methoxide (SME), sodium hydroxide (NaOH), and a mixture thereof, and the catalyst is input in a state of being dissolved in a sulfoxide-based solvent.

In the present invention, the heterogeneous linear carbonate means a carbonate of a different species from the dimethyl carbonate, specifically, a symmetric linear carbonate and an asymmetric linear carbonate, and more specifically, ethyl methyl carbonate (EMC) and diethyl carbonate (DEC).

The preparation of the ethyl methyl carbonate and the diethyl carbonate is not limited, and may be performed in a method using a reactive distillation column or in a method in which the reaction is performed in a continuous stirred tank reactor (CSTR) and distillation is performed in the distillation column, and specifically, since the composition of ethyl methyl carbonate and diethyl carbonate is determined through a ratio of dimethyl carbonate and ethanol, which is an equilibrium reaction, when the ratio of initially input dimethyl carbonate and ethanol is fixed, the transesterification reaction may be performed in a CSTR so that ethyl methyl carbonate and diethyl carbonate can be easily produced in a desired composition ratio.

This is because, in the case of reactive distillation, since a ratio of dimethyl carbonate and ethanol changes for each stage, a difficult operation is required to obtain ethyl methyl carbonate and diethyl carbonate in a desired composition ratio.

In the CSTR, the dimethyl carbonate and ethanol undergo an exchange reaction in the presence of a transesterification catalyst, from which a desired product can be obtained. More specifically, when dimethyl carbonate, ethanol, and a catalyst, which are raw materials for preparation, are continuously supplied to the CSTR, reaction products produced in the reactor are discharged as an effluent stream, and then introduced into a distillation column to selectively separate and obtain ethyl methyl carbonate and diethyl carbonate as desired products.

Catalysts used in the transesterification reaction may generally be one or more selected from the group consisting of lithium methoxide (LME), lithium ethoxide (LEE), sodium methoxide (SME), sodium hydroxide (NaOH), and a mixture thereof, and specifically, may be one or more selected from the group consisting of sodium methoxide (SME), sodium hydroxide (NaOH), and a mixture thereof having excellent activity.

However, as described above, these catalysts have low solubility in organic solvents and do not dissolve in dimethyl carbonate as a reaction raw material, ethyl methyl carbonate or diethyl carbonate as a desired product, so that there was a problem that caused column plugging in a reaction process or a purification process.

Accordingly, the inventors of the present application, as a result of in-depth contemplation of a method for effectively solving this problem, when the catalyst is input in a state of being dissolved in a polar solvent having excellent solubility, it was found that, by solving this problem, the catalyst is hardly precipitated, maintenance costs are reduced, and the catalyst can be reused, thereby exhibiting excellent economic efficiency.

In this case, the polar solvent may be a sulfoxide-based solvent, and specifically, the sulfoxide-based solvent may be represented by Chemical Formula 1 below.

$$R^1—S(=O)—R^2 \qquad \text{[Chemical Formula 1]}$$

in Chemical Formula 1, $R^1$ and $R^2$ are each independently a substituted or unsubstituted $C_1$-$C_{10}$ alkyl, $C_3$-$C_8$ cycloalkyl, heterocycloalkyl, aryl, or heteroaryl group.

More specifically, the $R^1$ and $R^2$ may be dimethyl sulfoxide (DMSO).

The dimethyl sulfoxide has high solubility in the catalysts. Therefore, when the catalyst is dissolved in the solvent and used, precipitation of the catalyst can be prevented, and thus, the plugging problem can be effectively solved.

In addition, since the catalyst dissolved in the solvent does not precipitate, the catalyst can be reused immediately after obtaining a desired product through a purification process, which is more preferable because process efficiency is increased in a continuous reaction process.

Such a catalyst may be input in a dissolved state in the sulfoxide-based solvent in an amount of 0.1% by weight or more and 3% by weight or less, specifically 0.1% by weight or more and 2% by weight or less, and more specifically 0.5% by weight or more and 1% by weight or less.

That is, based on the total weight of the solution in which the catalyst is dissolved in the solvent, an amount of the catalyst in the solution is 0.1% by weight or more and 3% by weight or less, specifically 0.1% by weight or more and 2% by weight or less, and more specifically 0.5% by weight or more and 1% by weight or less.

Outside the above range, when wt % of the catalyst is too high, it is not completely dissolved in the sulfoxide-based solvent, and the problem of precipitation is still present in a subsequent process, which is undesirable, and when wt % of the catalyst is too low, the total amount of input solvent increases, and thus reaction efficiency may decrease, which is not preferable.

An amount of these catalysts used may be 0.001% by weight or more and 3% by weight or less, specifically 0.001% by weight or more and 1% by weight or less, and more specifically 0.001% by weight or more and 0.1% by weight or less, based on the weight of dimethyl carbonate.

Outside the above range, when the content is too small, the reaction does not proceed efficiently, and when excessive content is input, the amount of input catalyst is increased even though an amount of unused catalyst is large, which is not preferable in terms of economics.

Meanwhile, dimethyl carbonate included as a reaction raw material can be commercially purchased and used, and may be those obtained by a gas phase catalytic reaction of carbon monoxide and nitrite ester, those obtained by reacting carbon dioxide and an alcohol under a solid catalyst, and dimethyl carbonate produced by a known method.

As another reaction raw material, commercially available ethanol can be used as it is, but it is preferable to use ethanol having a moisture content of 0.20% by mass or less (2000 ppm or less) so as not to affect the transesterification reaction of the present invention. Here, the removal of the contained water is performed by dehydration operation or the like with a drying agent such as, for example, a molecular sieve, anhydrous magnesium sulfate and/or calcium oxide.

An amount of ethanol used may be 20 to 150% by weight or less, specifically, 30 to 130% by weight or less, more preferably 40 to 130% by weight, based on the weight of dimethyl carbonate.

When the amount of input ethanol is too small, the reaction does not proceed efficiently, on the other hand, when the amount is too much, the complexity of removing the ethanol after the reaction increases, and is also not preferable in terms of economics.

Meanwhile, a reaction temperature of the transesterification reaction is influenced by the temperature in the reactor. The reaction temperature may be 30 to 130° C. or less, specifically, 60 to 120° C. or less, more specifically 80 to 100° C. or less, and therefore, the temperature in the reactor may also be adjusted to this temperature range.

Outside the above range, when the reaction temperature is too low, the reaction is not easily performed and the reaction efficiency is low, and when the reaction temperature is too high, energy costs increase and an amount of reaction by-products increases, which are not preferable.

In addition, the pressure of the reaction is not particularly limited, and may vary depending on the reaction temperature and reaction composition, and may be, for example, normal pressure to 1000 kPa.

In this way, when the transesterification reaction is completed in the reactor, the reaction concentrate including ethyl methyl carbonate and diethyl carbonate are obtained as an effluent stream. In addition, when this is filtered through a filter and then subjected to distillation, high purity ethyl methyl carbonate and diethyl carbonate can be obtained.

In addition, according to the present invention, when the catalyst is input in a state of being dissolved in a sulfoxide-based solvent, a precipitation amount of the catalyst is significantly reduced, thereby solving the plugging problem and enabling the reuse of the catalyst, resulting in excellent economic efficiency.

Hereinafter, examples will be given to describe the present invention in detail. However, the examples according to the present invention may be modified in various other forms, and the scope of the present invention is not to be construed as being limited to the examples described below. The examples of the present specification are provided to more completely explain the present invention to those of ordinary skill in the art.

EXAMPLE 1

135.12 g of dimethyl carbonate (DMC), 90.16 g of ethanol (EtOH), and 13.5 g of a sodium methoxide solution (SME, 1 wt % in dimethyl sulfoxide (DMSO)) as raw materials were reacted by stirring at a rate of 200 rpm at 70° C. and 1 bar for 1 hour.

In order to confirm the effect of the present invention through a simple experiment, the raw materials were reacted using a batch reactor, and ethyl methyl carbonate and diethyl carbonate were synthesized.

EXAMPLE 2

Ethyl methyl carbonate and diethyl carbonate were synthesized in the same manner as in Example 1, except that 13.5 g of a sodium hydroxide solution (NaOH, 1 wt % in dimethyl sulfoxide (DMSO)) was applied instead of 13.5 g of a sodium methoxide solution (SME, 1 wt % in dimethyl sulfoxide (DMSO)).

EXAMPLE 3

The raw materials were stirred and reacted as in Example 1 using 13.5 g of a sodium hydroxide solution (NaOH, 1 wt % in dimethyl sulfoxide (DMSO)).

ethanol (EtOH)) was applied instead of 13.5 g of a sodium methoxide solution (SME, 1 wt % in dimethyl sulfoxide (DMSO)).

COMPARATIVE EXAMPLE 2

Ethyl methyl carbonate and diethyl carbonate were synthesized in the same manner as in Example 1, except that 13.5 g of a sodium hydroxide solution (NaOH, 1 wt % in ethanol (EtOH)) was applied instead of 13.5 g of a sodium methoxide solution (SME, 1 wt % in dimethyl sulfoxide (DMSO)).

EXPERIMENTAL EXAMPLE 1

Qualitative and quantitative analyses were performed on the consumption of dimethyl carbonate as a raw material for preparation and amounts of ethyl methyl carbonate and diethyl carbonate as desired products in Examples 1 to 3 and Comparative Examples 1 and 2, and results are shown in Table 1 below.

For the qualitative and quantitative analyses, after passing the obtained compound through a filter, 1 g of a product passed through the filter was taken and mixed with 0.1 g of m-xylene, and then the concentration was measured using gas chromatography (GC) (YL6500GC manufactured by YOUNG IN Chromass Co., GC column: DB-1 30 m×0.53 mm, GC detector: FID). In addition, a reaction conversion rate of dimethyl carbonate as a raw material for preparation was calculated as mol % based on a consumption amount compared to an amount used, and the reaction selectivity of ethyl methyl carbonate and diethyl carbonate as desired products was calculated as mol % based on a total content of ethyl methyl carbonate and diethyl carbonate respectively produced.

In addition, after distilling the reaction concentrate generated after the reaction, residues were filtered using a 0.45 μm syringe filter, and then a weight of solid particles remaining in the filter was measured. The results are shown in Table 1 below.

TABLE 1

| | Classification | Example 1 | Example 2 | Example 3 | Comparative Example 1 | Comparative Example 2 |
|---|---|---|---|---|---|---|
| Activity results | DMC conversion rate [%] | 65 | 66 | 64 | 63 | 64 |
| | EMC selectivity [%] | 74 | 73 | 75 | 76 | 73 |
| | DEC selectivity [%] | 26 | 27 | 25 | 24 | 27 |
| Amount of solid catalyst in residue [g] | | 0.017 | 0.015 | — | 0.127 | 0.122 |

Then, the reaction concentrate produced after the reaction was distilled, 135.12 g of dimethyl carbonate (DMC) and 103.66 g of ethanol (EtOH) were input again as the same raw materials using the residue, and reacted by stirring under the same conditions.

COMPARATIVE EXAMPLE 1

Ethyl methyl carbonate and diethyl carbonate were synthesized in the same manner as in Example 1, except that 13.5 g of a sodium methoxide solution (SME, 1 wt % in According to Table 1, when the reaction is performed by the method according to the present invention, it can be confirmed that the activity of the catalyst is the same as in the case of the conventional method, but the precipitation of the catalyst is significantly reduced and there is almost no precipitation, and, as can be seen from Example 3, since almost the same activity can be obtained even when the catalyst is reused, the reuse efficiency is very excellent.

The invention claimed is:

1. A method of preparing ethyl methyl carbonate (EMC) and diethyl carbonate (DEC), comprising performing a transesterification reaction of dimethyl carbonate (DMC) and ethanol (EtOH) in the presence of a catalyst, wherein the catalyst is one or more selected from the group consisting of lithium methoxide (LME), lithium ethoxide (LEE), sodium methoxide (SME), sodium hydroxide (NaOH), and a mixture thereof, and
the catalyst is input in a state of being dissolved in a sulfoxide-based solvent.

2. The method of claim 1, wherein the catalyst is one or more selected from the group consisting of sodium methoxide (SME), sodium hydroxide (NaOH), and a mixture thereof.

3. The method of claim 1, wherein the sulfoxide-based solvent is represented by Chemical Formula 1 below:

$$R^1—S(=O)—R^2 \qquad \text{[Chemical Formula 1]}$$

in Chemical Formula 1,
$R^1$ and $R^2$ are each independently a substituted or unsubstituted $C_1$-$C_{10}$ alkyl, $C_3$-$C_8$ cycloalkyl, heterocycloalkyl, aryl, or heteroaryl group.

4. The method of claim 3, wherein the sulfoxide-based solvent is dimethyl sulfoxide (DMSO).

5. The method of claim 1, wherein the catalyst is input in a state of being dissolved in the sulfoxide-based solvent in an amount of 0.1% by weight or more and 3% by weight or less.

6. The method of claim 1, wherein the catalyst is input in an amount of 0.001% by weight or more and 3% by weight or less, based on a weight of dimethyl carbonate.

7. The method of claim 1, wherein the transesterification reaction is performed in a continuous stirred tank reactor (CSTR).

* * * * *